United States Patent
Rom

(10) Patent No.: US 6,685,637 B1
(45) Date of Patent: Feb. 3, 2004

(54) ULTRASONIC DIAGNOSTIC IMAGING SYSTEM WITH MULTIPLE LANGUAGE USER INTERFACE

(75) Inventor: George Daniel Rom, Stoneham, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/269,284

(22) Filed: Oct. 11, 2002

(65) Prior Publication Data (65)

(51) Int. Cl.$^7$ .............................................. A61B 8/00
(52) U.S. Cl. ..................................................... 600/437
(58) Field of Search ............................... 600/437, 440, 600/459, 443, 460, 447; 704/8; 710/5, 8; 395/600; 717/11; 705/2

(56) References Cited

U.S. PATENT DOCUMENTS

| | | | | |
|---|---|---|---|---|
| 5,734,882 A | * | 3/1998 | Lopresti et al. | 707/200 |
| 6,094,689 A | * | 7/2000 | Embry et al. | 710/5 |
| 6,163,816 A | * | 12/2000 | Anderson et al. | 710/8 |
| 6,205,418 B1 | * | 3/2001 | Li et al. | 704/8 |
| 6,213,944 B1 | * | 4/2001 | Miller et al. | 600/437 |
| 6,272,469 B1 | * | 8/2001 | Koritzinsky et al. | 705/2 |
| 6,289,513 B1 | * | 9/2001 | Bentwich | 717/106 |
| 6,436,040 B1 | * | 8/2002 | Collamore et al. | 600/437 |
| 6,468,212 B1 | * | 10/2002 | Scott et al. | 600/437 |
| 6,491,630 B1 | * | 12/2002 | Saccardo et al. | 600/437 |

OTHER PUBLICATIONS

HDI 3500 Ultrasound System Reference Manual, 4703–0036–01 Rev B, 6/99, pp. iii–iv, 3-4—3-5, ATL Ultrasound, a Philips Company.

HDI 4000 Ultrasound System Reference Manual, 4703–0037–01 Rev A, May 2002, pp. vi, 106, and explanatory page with two screen shots, Philips Medical Systems.

* cited by examiner

Primary Examiner—Dennis W. Ruhl
Assistant Examiner—Ruby Jain
(74) Attorney, Agent, or Firm—W. Brinton Yorks, Jr.

(57) ABSTRACT

An ultrasonic diagnostic imaging system is described which enables the system operator to change the language of the graphical user interface without the need to restart the system. The software build for text, dialog boxes, symbols, icons, and other language-specific information contains this display information in multiple languages. By accessing a setup menu or other selection screen the user can change to one of the other languages stored on the system, preferably including all language-specific features. In the describe embodiments this change many be implemented without the need to reboot the system. In one embodiment the user has the ability to select multiple languages for different functions such as one language for system operation and another language for diagnostic reports.

17 Claims, 5 Drawing Sheets

ULTRASONIC DIAGNOSTIC IMAGING SYSTEM WITH MULTIPLE LANGUAGE USER INTERFACE

This invention relates to medical diagnostic imaging systems and, in particular, to ultrasonic diagnostic imaging systems which present or produce diagnostic information in various languages.

Medical imaging systems such as ultrasonic diagnostic imaging systems are in use in most of the countries of the world. Accordingly, these systems should respond to a user in the local language of his or her country. Some local manufacturers produce imaging systems which are distributed in only the local country, in which case the system can be produced with control, display and output capabilities in only the language of the country of manufacture. However many suppliers produce imaging equipment for inter-country or worldwide distribution, in which case the systems must be capable of operating in multiple languages. In some regions of the world such as Europe, certain language requirements are mandated for medical equipment. These mandates may state language requirements for operator manuals, system controls, system text and messages, or various combinations thereof. For example, a mandate may require text messages pertaining to patient safety or system faults to be displayed in the local language, so that they are clearly and immediately understood by the operator. International manufacturers therefore must produce imaging equipment with the ability to change the language used for the controls and displays of the imaging system, as well as the language of system output such as image graphics and reports.

The selection of the language in which an imaging system is to operate is generally made at the time of manufacture. The customer may be asked to specify the language in which the system is to operate, in response to which the manufacturer will install software which presents displays, character fonts, and reports in the desired language. Other parts of the system, including operating manuals, control panels and keyboards may also be customized for a particular country and/or language. Once the system is shipped and installed at a customer's site, however, changing the system for operation in a new language can become more problematic. Customized language-specific hardware such as control panels and keyboards must often be replaced when a change in language is required. A change in the graphical user interface can require the shipment of new software to a local serviceperson, who will install and verify correct operation of the new software running in the new language. It is possible for multiple languages to be resident on the imaging system so that the user can change the system language without a service call, but usually a change can only be performed by rebooting or restarting the system, which utilizes time to shut down and restart the system and interrupts the ongoing diagnostic examination. Accordingly it is desirable to better facilitate the modification of an imaging system to operate in a different language, and in particular to allow the operator to make such changes without the need for a service call or system shutdown.

In accordance with the principles of the present invention, an ultrasonic diagnostic imaging system is provided which contains software for operating the graphical user interface in different languages. The user is able to access a setup screen while the system is operating and select a different language to be used on the graphical user interface. To make the new language active the user may be required to relog into the system. In a preferred embodiment the new language becomes active without the need to log into the system again. In accordance with a further aspect of the present invention, the user can select the capability to operate the user interface in one language and produce output such as diagnostic reports in a second language.

Figure 1:
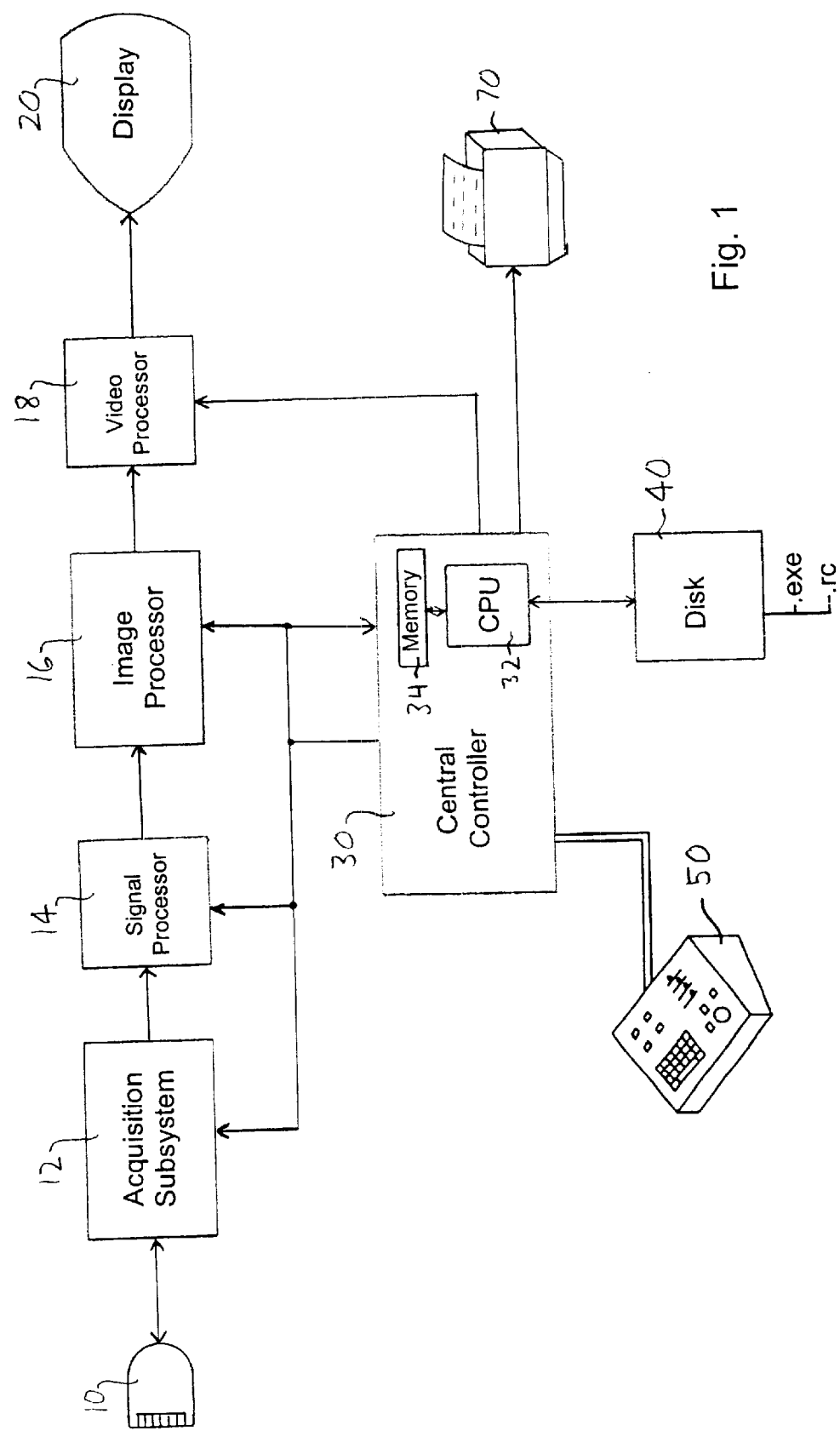
FIG. 1 illustrates in block diagram form the system architecture of a diagnostic ultrasonic imaging system which is constructed in accordance with the principles of the present invention to be selectively operable in different languages.

Referring first to FIG. 1, a diagnostic ultrasonic imaging system is shown in block diagram form. A transducer probe 10 is controlled by an acquisition subsystem 12 to transmit ultrasonic energy into the body of a patient and to receive echoes from the anatomy of the patient. The acquisition subsystem actuates elements of the transducer of the probe at specific times and frequencies so as to transmit beams of ultrasound into the body. The resulting echoes are received by one or more transducer elements of the probe 10 and coupled to the acquisition subsystem where, in the case of an array transducer, the receive beams are steered and focused to produce coherent echo signals associated with the time-related locations from which they were received. The beams of echo signals are applied to a signal processor 14 which refines the signals by selective filtering, speckle reduction, harmonic separation, and other known processing techniques. The signals are also detected by amplitude detection, phase detection, Doppler power or frequency shift detection, and other known techniques which extract the desired display information from the received signals. The processed signals are applied to an image processor 16 which uses the signals to produce a two or three dimensional display of the desired format. e.g., a rectilinear or sector display, B mode display, spectral or colorflow Doppler display, three dimensional rendering, and so forth. The processed image is coupled to a video processor 18 which produces raster scan signals as required by the display device 20 of the system This is the path by which a diagnostic image, in this case an ultrasound image, is acquired and displayed. In other imaging modalities such as CT systems, nuclear cameras, and MRI systems the probe and acquisition subsystem will be replaced by elements unique to those modalities such as photomultiplier tubes, scintillation crystals, r.f. and gradient coils, and the like.

In the embodiment of FIG. 1 diagnostic image acquisition is controlled by a central controller 30 which is coupled to the elements of the image signal path. The central controller is coupled to a control panel 50 by which the user controls the ultrasound system. Control is effected by hard keys and switches on the control panel. For example the user may manipulate time gain control slides or a gain control knob on the control panel to adjust and improve the processing of echo signals performed by the acquisition subsystem. Control of the imaging system is also effected by softkeys, keystroke entry, and menu and graphics manipulation on a graphical user interface (GUI) displayed on the display 20. While the graphical user interface may be produced and controlled by a specialized graphics card in the diagnostic imaging system, in the embodiment of FIG. 1, which depicts a p.c.-based system, the GUI is produced and constantly updated by an operating system running on a CPU 32 of the central controller 30. During runtime the operating system software and programs and data files needed by the operating system are stored in the memory 34 accessed by the CPU. The central controller is coupled to the video processor 18 which overlays the diagnostic image over the graphical user interface provided by the CPU 32 and can display both in a single display frame. The user may manipulate a pointer or cursor on the GUI, for instance, to select a probe type or display mode such a colorflow or spectral Doppler. The user can use the keyboard on the control panel 50 to enter patient information on the GUI screen. The user may manipulate the GUI pointer to indicate areas of the image where borders are to be defined or measurements made, for example, such as heart wall boundaries or fetal gestational age.

After reviewing and analyzing the images and diagnostic information produced by the system the user may decide to prepare a report of his diagnosis. Ultrasound and other imaging systems generally include report generation capabilities by which the information gathered and produced by the system as well as selected images are presented in a report format which may be transmitted over a network to a recipient or printed out on a printer 70.

The graphical user interface will generally contain a significant amount of information which is unique to a certain language or culture. For instance, softkeys on the display screen may have text labels defining their functions, as will the text on lines of pull-down menus, which should be localized to the language of the user. Textual screen or tool tips may appear when the GUI pointer is pointed at a symbol on the screen, which should also be localized to the language being used. Dialog boxes which appear to guide the user or warn the user of potential problems such as data which needs to be saved will generally also contain text which needs to be localized. The user may want to measure certain anatomy in the image such as the head, abdomen or limbs of a developing fetus, The user may want to label the anatomy shown in an image such as "head", "forearm", or "kidney." Measurements and labels are other display information which should be localized. The text entered from the keyboard may need to include characters and inflection marks unique to the language used.

In addition, icons or symbols used in the GUI may differ from one language or culture to another. For example an exclamation point symbol may be used in an English language dialog box for a desired effect, but may not be desirable in the same dialog box of an Asian language system.

In accordance with the principles of the present invention the imaging system of FIG. 1 includes user interface elements localized to a plurality of different languages, which may be selected by the user. In one embodiment the data defining these display elements are contained in resource scripts or files (.rc files) stored on a disk 40, which is accessible to the CPU 32 running the operating system that generates the GUI. The disk 40 also stores programs or executables (.exe files) which execute and produce the GUI display. The .rc files hold strings (identified text which can be displayed on the screen), dialog box files, bit maps, and cursor and icon data files, as well as other types of data. The databases of the .rc file are generally written in a base language, such as English, French, German or Italian. The base language database is then translated into the other languages which the system is to support. The translated databases are then associated with the GUI executables.

One way to make this association is to build a separate set of executables for each language during the software build process. For instance, the build process would combine a set of executables with a German .rc file to create a German language executable set, the executables would be combined with an English .rc file to create an English language executable set, and so forth. The result is a set of executables for each language. While this approach produces the intended result, a system for which the user can change languages, there are several drawbacks. One is that the executables are replicated for each language, resulting in large file sizes which require a large amount of disk space on the system. Coordination of the build process is complex and must be managed carefully. This approach generally requires that the user restart or reboot the system before a newly selected language takes effect. As a result, the user must close all applications and restart the imaging system each time a language is changed. It is generally not possible to change the language "on the fly," during runtime.

Another approach which will achieve the intended result is to translate only the string (text) tables from the .rc files and build all of the .rc files for the different languages into one set of executables. As a result, for instance, a measurement module would contain a measurement in each of the languages from each of the .rc files. While this approach presents all of the text of the GUI in the local language, it does not provide other refinements to tailor the system to the local language. For instance, since the dialog box files are not translated or otherwise modified, the same set of dialog boxes is used for each language. This means that the dialog boxes must be sized to accommodate the languages with the longest displayed text strings; the dialog boxes will appear to be incorrectly sized when displayed with languages with short text strings. The inability to customize the dialog boxes also means that right-to-left languages such as Hebrew and Arabic are poorly displayed. A similar problem is presented by vertically arrayed languages such as Japanese. Accordingly it may be desirable to use a variation of this approach, in which the dialog boxes are also translated so as to be correctly sized for each language. While the file storage requirements in this approach are reduced compared to the previous approach and the build process is generally smoother, it is still generally necessary to restart the system when changing languages in this approach.

In a preferred embodiment of the present invention, the executables are developed with the requirement that, each time a textual graphic or symbol is drawn on the screen, the program accesses the .rc file of the currently selected language. Each time the GUI is redrawn on the screen, the appropriate language string is accessed from the proper .rc file by the operating system display interface and put in the active buffer (memory) where it is used for display. Thus, the correct language text, properly sized dialog boxes, and proper symbols are displayed each time the GUI is drawn. A benefit of this approach is that the language can be changed on the fly. When the user selects a new language and returns to the application running on the system, he will find that the language of the GUI changed to the new language during a previous GUI refresh.

Another implementation of the same approach is to create a language-specific data set for each language-dependent display element. The operating system would then access the appropriate data set for the currently selected language. For example the display data sets can be defined as .dll files. The .dll file for a specific measurement term might be meas.dll. In this implementation a different .dll file is defined for each language such as meas_enu.dll, meas_frf.dll, meas_deu.dll, and so forth, where the first file displays the measurement in English (US), the second file displays the measurement in French (France), the third file displays the measurement in German (Germany), etc. The .dll files are added to the executables during the build process.

Figure 4:
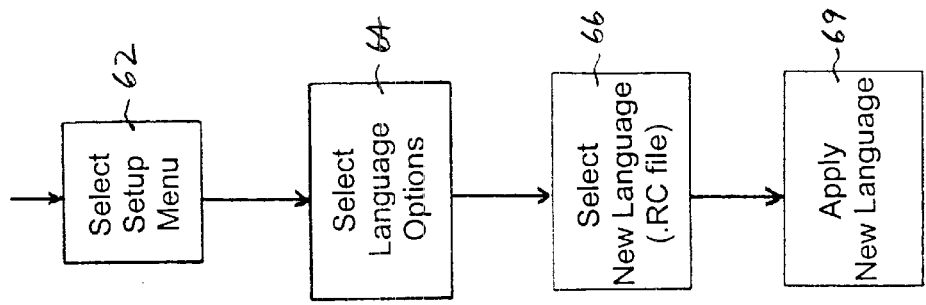
FIG. 4 illustrates a flowchart for changing the language of an imaging system graphical user interface in accordance with the present invention which allows the language to be changed during run time of the current system application.
Figure 3:
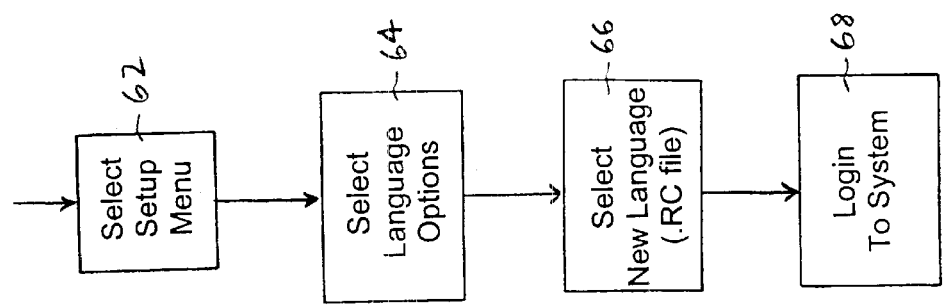
FIG. 3 illustrates a flowchart for changing the language of an imaging system graphical user interface in accordance with the present invention which requires the operator to log into the system to implement the change.
Figure 2:
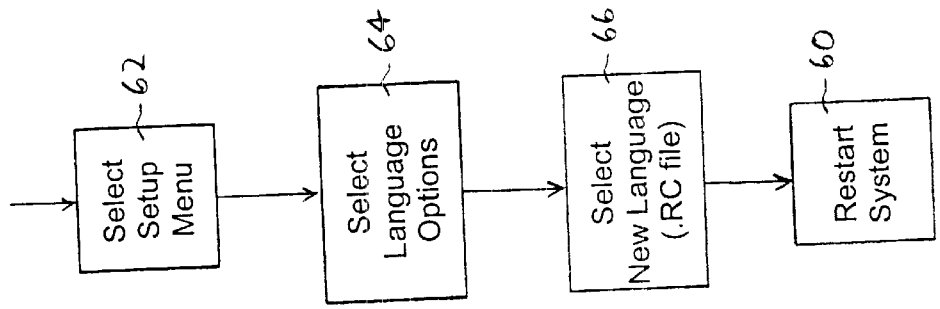
FIG. 2 illustrates a flowchart for changing the language of an imaging system graphical user interface which requires the system to be restarted to implement the change.

The steps for changing the language of the above embodiments are outlined in FIGS. 2, 3, and 4. Preferably, the GUI is designed to enable the user to access a Setup screen at any time. In step 62 of FIG. 2 the user accesses the Setup menu and selects the language options of the menu (step 64). The user then selects the new language (step 66) which, when invoked, causes the operating system to access a different executable set, .rc file, or other data source containing the new language data. For the embodiments above where it is necessary to restart the system in order to make the selection effective, the user will be prompted to close his applications and restart the imaging system for the change to take effect. The user then restarts the system (step 60).

FIG. 3 shows a more efficient sequence than that of FIG. 2, which avoids the need to restart the imaging system. In this sequence the Setup menu is accessed, the language options selected, and the new language selected as before. However in this embodiment it is not necessary to restart the system to invoke the new language, but only to log in to the system. This saves the time required to reboot the operating system. When the user logs in again (step 63), the new language takes effect.

FIG. 4 shows a typical preferred sequence in which it is not necessary to restart or log into the system to invoke the language change. In this embodiment the user accesses the Setup menu, selects the language options and selects the new language and its .rc file, .dll file set, or other language data set. After the selection is made the user makes the selection to apply the new language (step 69), which may be by selecting a softkey on the GUI, using a key on a keyboard, or clicking or double clicking a trackball or mouse button. The user can then return to his application, which is now running in the newly selected language. The language change is made on the fly, without requiring a halt to the ongoing diagnostic exam.

Figure 5:
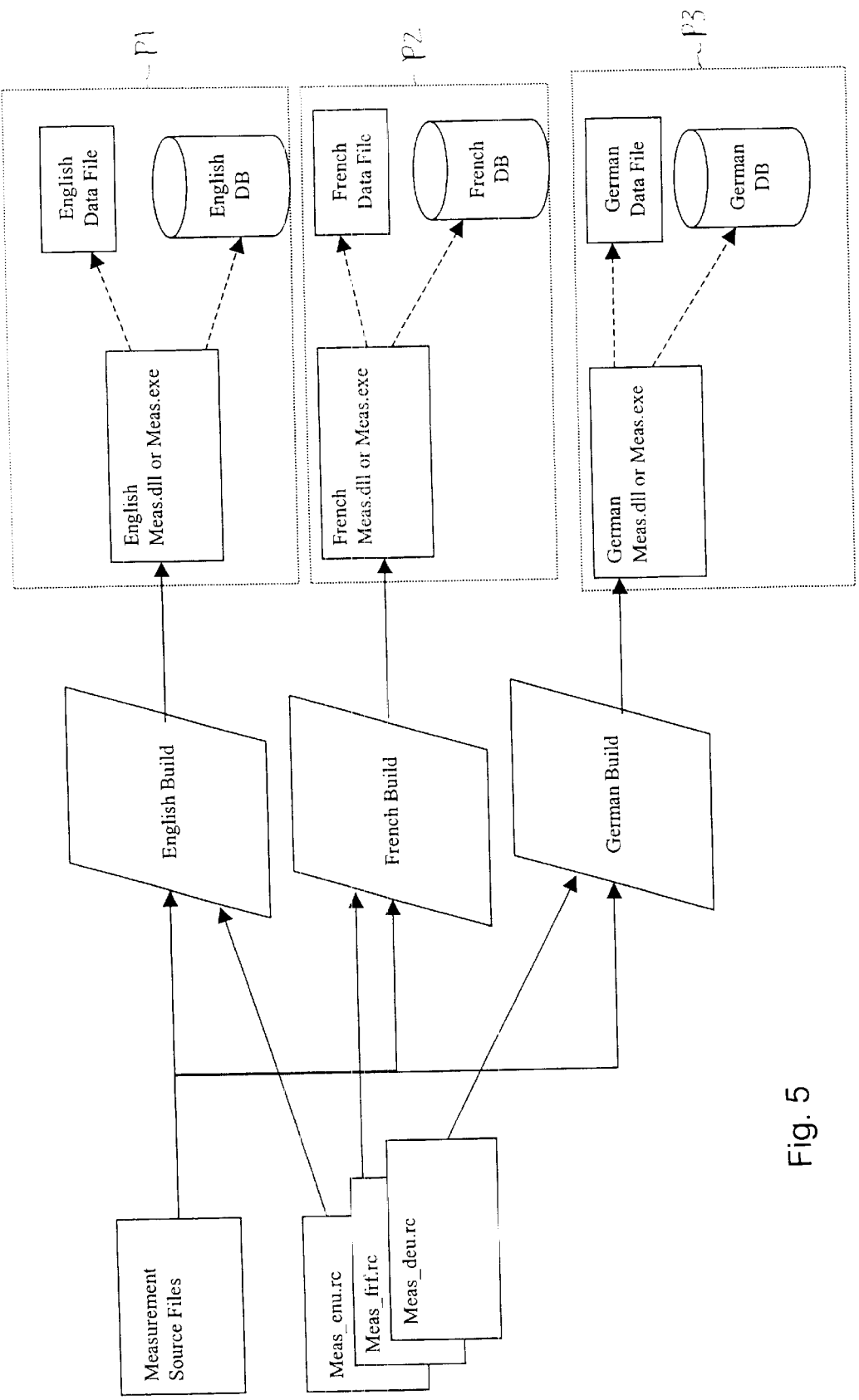
FIGS. 5, 6, and 7 illustrate different software build processes which may be used in embodiments of the present invention.
Figure 6:
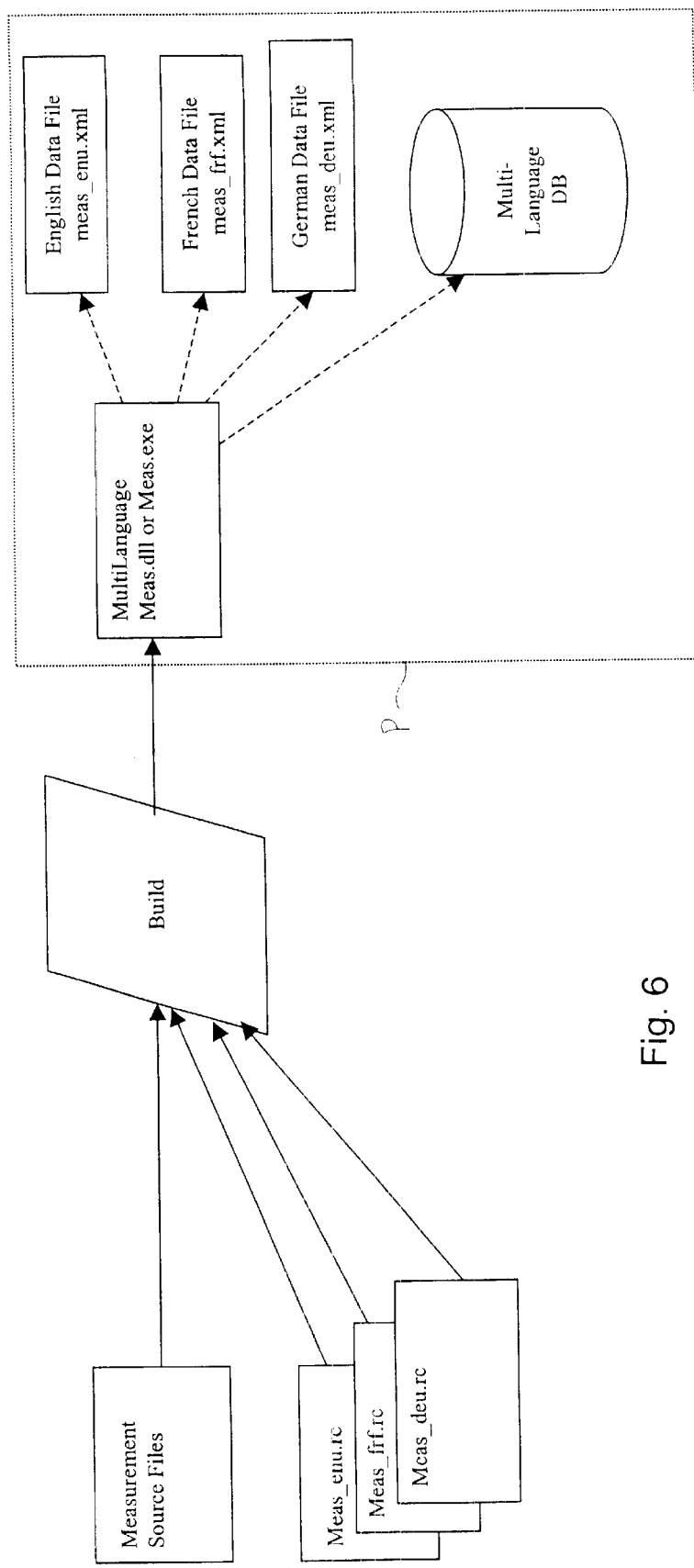
Figure 7:
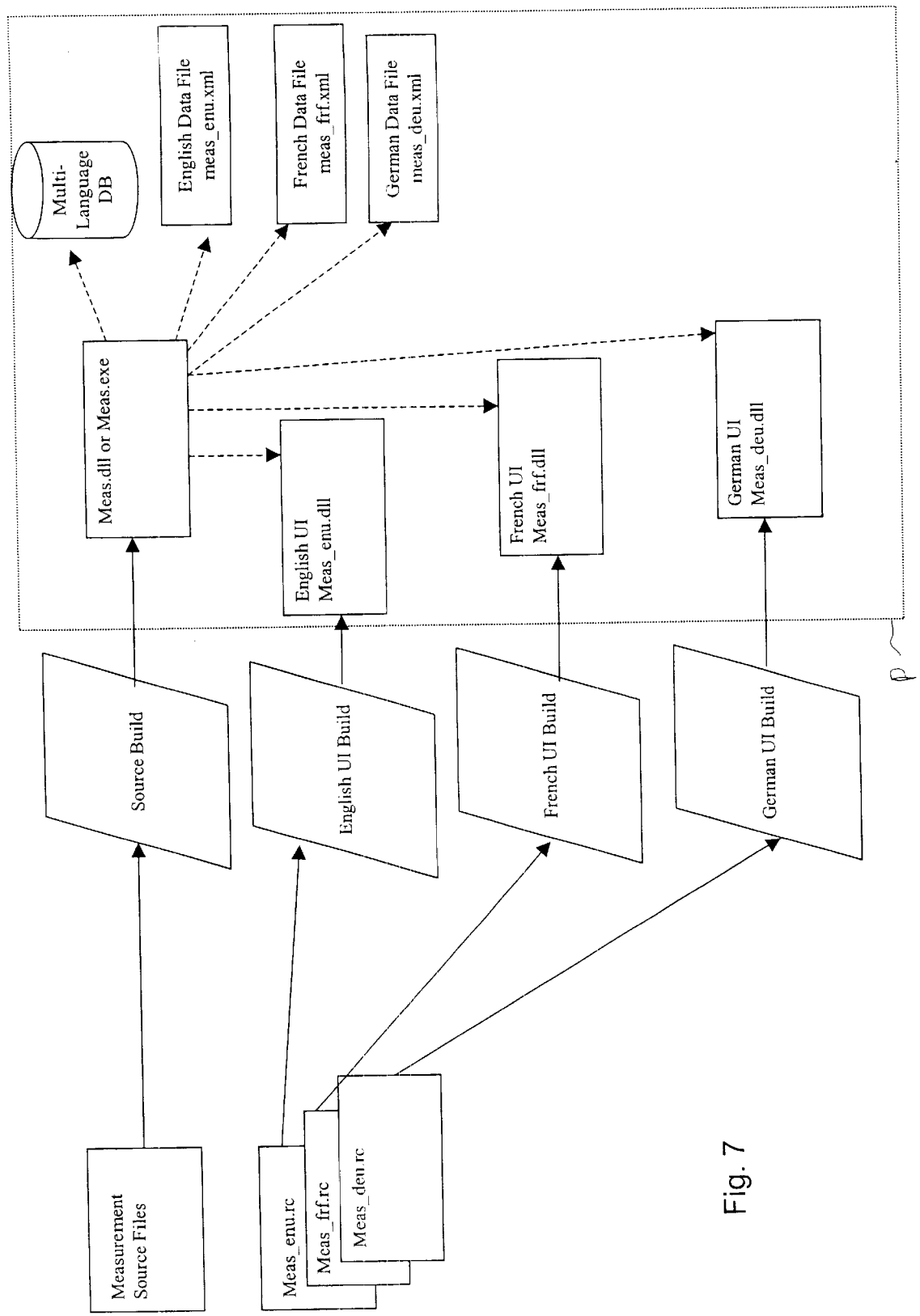

Software build processes which may be used in the implementation of the various embodiments of the present invention are shown in block diagram form in FIGS. 5, 6, and 7. In these drawings the rectangles represent software modules such as code, executables and data. The parallelograms represent tasks. The dashed arrows represent associations that are made at runtime, for example, an executable or .dll file accessing a data file at runtime or loading another .dll file or looking up values in a database (DB). The boxes labeled "P" at the right side of each drawing represent software packages that are included in ultrasound systems. All of these drawings show three sources of translatable items: .rc files which become part of the executable, data files such as .xml or .html report templates, and a database of separate sets of tables for each language.

FIG. 5 illustrates the situation where a customer orders an ultrasound system which operates in a particular language. In that case, a software package P1 or P2 or P3 is built in the chosen language (e.g., English, French, or German). The customer received the ultrasound system with the ordered software package installed and operational.

FIGS. 6 and 7 illustrate situations in which the ultrasound system is supplied with multiple languages which can be selected without the need to restart the ultrasound system. In FIG. 5 all of the languages are built into one multi-language package, resulting in all of the languages being loaded at runtime. The configuration of FIG. 6 is more flexible as the different languages can be partitioned so that packages with a fewer or greater number of languages can be readily created. In addition the executable is smaller at runtime since only one language, the one selected by the user, is loaded at a time. Additional languages can be added to the system at a later time without recompiling or linking the source files.

The above described embodiments may be implemented with or without a keyboard change. The same keyboard may be used for different languages by remapping some or all of the keys for the symbols of each language. For certain languages, changing to a different logical keyboard layout on the fly may be desirable or useful, for example, to better facilitate searches in the online "Help" files of the language or to better facilitate text entry in the local language.

In accordance with another aspect of the present invention, the imaging system is designed to use different languages for different functions during the same application. For example, a French-speaking doctor in a hospital in Switzerland may be examining a patient referred to him by a German-speaking physician in another locale in Switzerland. The examining doctor may want to conduct the diagnostic exam in French, then send a German diagnostic report to the referring physician. The imaging system is then configured to operate entirely in the French language, except that the system output, the diagnostic report, is to be produced in German. This may be configured by the Setup menu, which can give the user the choice of selecting a different language for reporting than that for general system operation. Alternatively, a report-generation screen can present a language choice option at the time the report is prepared or finished or transmitted over a network or printed. In such an embodiment the French doctor would select French as the language for system operation, and German as the language for the diagnostic report. The report could always be produced in German, but in a particular embodiment it may be desirable to enable the French doctor to prepare the report in French, then to have the system change the language to German for the printed copy or the copy that is sent electronically to the referring German-speaking physician over a network.

In addition to localizing the language of the imaging system, an embodiment of the present would also localize other locale information such as date format, decimal separator, time format, time zone, and other locale-specific data.

What is claimed is:

1. A medical diagnostic imaging system having multiple language display capability which can be selectively controlled by a user, wherein a language is a body or system of words and phrases used by a large community or by a people, a nation, or a group of nations, comprising:

a graphical user interface which displays both a diagnostic image and language-specific information;

a plurality of language data files for different languages stored on the imaging system;

a user control which is operable to select one of the different languages; and a control which is actuatable to cause the graphical user interface to diplay non-patient ID information in a selected language without restarting the imaging system.

2. The medical diagnostic imaging system of claim 1, further comprising an operating system which runs on the imaging system for the generation of the graphical user interface, wherein the control which is actuatable to cause the graphical user interface to display information in a selected language comprises a control which causes the graphical user interface to display information in a different language without restarting the operating system.

3. The medical diagnostic imaging system of claim 1, wherein the graphical user interface further comprises a login function by which a user can log onto the imaging system, wherein the control which is actuatable to cause the graphical user interface to display information in a selected language comprises the login function.

4. The medical diagnostic imaging system of claim 1, wherein the user control which is operable to select one of the different languages comprises a language selection menu by which a user can select one of a plurality of different languages, wherein the control which is actuatable to cause the graphical user interface to display information in a selected language comprises the language selection menu.

5. The medical diagnostic imaging system of claim 4, wherein selection menu further comprises a user selection which, when selected, causes the graphical user interface to change to display of a newly selected language.

6. The medical diagnostic imaging system of claim 1, wherein the user control which is operable to select one of the different languages comprises a language selection menu by which a user can select one of a plurality of different languages, wherein the imaging system further comprises a user control panel having a plurality of user controls; and wherein the control which is actuatable to cause the graphical user interface to display information in a selected language comprises a user control of the control panel.

7. The medical diagnostic imaging system of claim 1, wherein the language data files are stored as data files capable of representing user interface elements.

8. The medical diagnostic imaging system of claim 1, wherein the language data files are stored as .dll files.

9. The medical diagnostic imaging system of claim 1, wherein the language data files further comprise dialog files which are different for different languages.

10. The medical diagnostic imaging system of claim 1, wherein the language data files further comprise symbol files which are different for different languages.

11. The medical diagnostic imaging system of claim 1, wherein the imaging system comprises an ultrasonic diagnostic imaging system.

12. The medical diagnostic imaging system of claim 1, wherein the graphical user interface displays image frames including both a diagnostic image and text in a specific language.

13. The medical diagnostic imaging system of claim 1, further comprising a keyboard which is operable to enter text in a plurality of different languages, wherein the logical keyboard layout is changed to a different native language layout in response to selection of a different language.

14. A medical diagnostic imaging system having multiple language display capability which can be selectively controlled by a user, wherein a language is a body or system of words and phrases used by a large community or by a people, a nation, or a group of nations, comprising:

a graphical user interface which displays language-specific information;

a plurality of language data files for different languages stored on the imaging system;

a user control which is operable to select a first one of the different languages for system operation and a second one of the different languages for system output.

15. The medical diagnostic imaging system of claim 14, wherein the system output comprises a diagnostic report.

16. The medical diagnostic imaging system of claim 14, wherein the user control comprises a menu display from which a user can select a first language for system operation and a second language for a diagnostic report.

17. The medical diagnostic imaging system of claim 15, wherein the user control comprises a first set of selections from which a user can select a first language for system operation and a second set of selections, associated with a diagnostic report, from which a user can select a second language for the diagnostic report.

* * * * *